United States Patent [19]

Kisner

[11] Patent Number: 4,521,287
[45] Date of Patent: Jun. 4, 1985

[54] HIGH RATE SPUTTERING OF EXHAUST OXYGEN SENSOR ELECTRODE

[75] Inventor: Howard D. Kisner, Wichita Falls, Tex.

[73] Assignee: General Motors Corporation, Detroit, Mich.

[21] Appl. No.: 625,846

[22] Filed: Jun. 28, 1984

[51] Int. Cl.³ .............................................. C23C 15/00
[52] U.S. Cl. .......................... 204/192 SP; 204/192 S; 204/192 C; 204/427
[58] Field of Search .......... 204/192 SP, 192 S, 192 C

[56] References Cited

U.S. PATENT DOCUMENTS

| | | | |
|---|---|---|---|
| 3,528,902 | 9/1970 | Wasa et al. | 204/192 |
| 3,844,920 | 10/1974 | Burgett et al. | 204/192 S |
| 3,878,085 | 4/1975 | Corbani | 204/192 |
| 4,046,660 | 9/1977 | Fraser | 204/298 |
| 4,136,000 | 1/1979 | Davis et al. | 204/192 S |
| 4,198,283 | 4/1980 | Class et al. | 204/298 |
| 4,204,936 | 5/1980 | Hartsough | 204/298 |
| 4,253,931 | 3/1981 | Gold et al. | 204/192 SP |
| 4,253,934 | 3/1981 | Berg et al. | 204/195 S |
| 4,264,647 | 4/1981 | Trevorrow | 204/192 S |
| 4,282,083 | 8/1981 | Kertesz et al. | 204/298 |
| 4,303,490 | 12/1981 | Gold et al. | 204/192 |
| 4,328,080 | 5/1982 | Harris | 204/192 EC |
| 4,400,255 | 8/1983 | Kisner | 204/192 SP |

OTHER PUBLICATIONS

Hieronymi et al., Thin Solid Films, 96(1982), pp. 241–247.
Chapin, Vacuum Technol., Jan. 1974.
Nyaiesh, Thin Solid Films, 86(1981), pp. 267–277.

*Primary Examiner*—Arthur P. Demers
*Attorney, Agent, or Firm*—Robert J. Wallace

[57] ABSTRACT

A method of sputtering a platinum exhaust gas electrode onto a vitrified zirconia thimble for an electrochemical-type exhaust gas oxygen sensor. Porous high surface area films are consistently deposited at high rates. A DC magnetron cathode assembly having a magnetic field strength of at least 500 gauss across its target face is used at a sputtering power of about 4–9 kilowatts. A thimble-target spacing of less than about 3.0 cm, a pressure less than about 10 millitorr, a sputtering atmosphere consisting essentially of more than about 50 percent nitrogen and/or oxygen, an electrically isolated deposition surface, and an electrically floating reference electrode precoated on the zirconia thimble surface are used.

4 Claims, 4 Drawing Figures

HIGH RATE SPUTTERING OF EXHAUST OXYGEN SENSOR ELECTRODE

FIELD OF THE INVENTION

This invention relates to solid electrolyte electrochemical type exhaust gas oxygen sensors. It more particularly relates to a high rate sputtering process for depositing a fast responding platinum exhaust electrode onto vitrified zirconia thimbles for such sensors.

BACKGROUND OF THE INVENTION

A typical automotive type solid electrolyte exhaust gas oxygen sensor is disclosed in U.S. Pat. No. 3,844,920 Burgett et al. It has a zirconia sensing element shaped as a tapered thimble. One end of the tapered thimble is open and has a thick circumferential flange. The other end is closed and forms the most active part of the element. The interior and exterior of the thimble each has a discrete porous electrode coating of platinum or the like.

The interior, i.e. reference or inner, electrode is exposed to a known source of oxygen, such as air or a mixed metal oxide, for establishing a reference electrode potential. This electrode is generally formed by thick film techniques, such as painting a coating of platinum ink onto the zirconia thimble, drying the coating, and then firing the coated thimble at an elevated temperature. An improved technique for applying the reference electrode, is disclosed in U.S. Pat. No. 4,264,647 Trevorrow.

The exterior, i.e. exhaust or outer, electrode is usually formed by thin film techniques, such as evaporation or sputtering. Improved sputtering techniques for applying the outer electrode are disclosed in U.S. Pat. Nos. 4,244,798 Gold et al; 4,253,931 Gold et al; and 4,303,490 Gold et al. Both Gold et al patents describe sputtering from a planar target that is part of a commercially available DC magnetron cathode assembly. They do so at a pressure of about 10-20 millitorr, preferably in an atmosphere of nitrogen and/or oxygen along with argon, a target-thimble spacing of at least about 3.0 cm, and at a high sputtering rate of 13-20 watts per cm$^2$ of target area, to provide fast responding sensors. U.S. Pat. No. 4,253,934 Berg et al describes increasing the yield of fast responding sensors by treating the electroded thimbles in substantially oxygen-free nitrogen at an elevated temperature. However, there was no practical way to discern a fast responding thimble from a slow responding thimble before assembly into the finished sensor. Accordingly, Berg et al proposed nitrogen aging all the thimbles before assembly into sensors. The increase in yield of fast responding sensors was sufficient to offset the cost of such a treatment.

In my U.S. Pat. No. 4,400,255 Kisner, I describe improving the foregoing techniques of sputtering from a planar target even further. I describe supporting the thimbles during sputtering in such a way that the inner and outer electrodes can be maintained at relatively different electrical potentials. In addition, I disclose providing a low resistance electrical path between the inner electrode and the sputtering anode.

I have now invented a new sputtering cathode assembly that is distinctly different from the planar target-cathode assembly previously referred to. It is described in my U.S. patent application Ser. No. 625,847 that is entitled "Magnetron Sputtering Cathode Assembly and Magnet Assembly Therefor" and filed concurrently herewith. My new sputtering cathode assembly provides faster platinum deposition and stronger heating than the planar DC magnetron cathode assembly previously used to deposit the exhaust electrode on the exhaust oxygen sensor. Moreover, I believe my new cathode assembly provides more uniform heating than the commercially available planar DC magnetron cathode assembly previously used. In brief, my new DC magnetron cathode assembly provides a considerably stronger magnetic field across the target face and a much stronger heating effect than attained with the planar DC magnetron cathode assembly previously used. I believe that its effects are more uniform too.

My new DC magnetron cathode assembly must be used in a new way if one wants high yields of fast responding exhaust electrodes when using it. This specification describes and claims the new process of using my new cathode assembly.

OBJECTS AND SUMMARY OF THE INVENTION

An object of this invention is to provide a new sputtering process for depositing platinum using my DC magnetron cathode assembly that is described and claimed in my concurrently filed U.S. patent application Ser. No. 625,847.

Another object of this invention is to provide a rapid process for producing high yields of fast responding platinum exhaust electrodes for zirconia-type exhaust gas oxygen sensors.

The invention comprehends sputtering platinum from a DC magnetron cathode assembly that has a magnetic field strength of at least 500 gauss as actually measured across its target face, and no significant electron shields. The platinum is sputtered onto an upstanding vitrified zirconia thimble in a predominantly nitrogen and/or oxygen atmosphere at a pressure of less than about 10 millitorr, a minimum target face-thimble closed end spacing of less than about 3.0 cm under a sputtering power of about 6-10 kilowatts. Deposition is obtained by moving the thimble past the target face at a rate slow enough to produce the desired coating thickness but fast enough to allow only a thin darkened region to form on the thimble surface beneath the coating, i.e. about 5-10 cm per minute. The highest yields of thimbles having an acceptable darkening are obtained by allowing the thimble reference electrode to electrically float to a higher potential than the thimble exhaust electrode during sputtering.

BRIEF DESCRIPTION OF THE DRAWING

Other objects, features and advantages of the invention will become more apparent from the following description of preferred examples thereof and from the drawing, in which.

DESCRIPTION OF THE PREFERRED EMBODIMENTS

Figure 1:
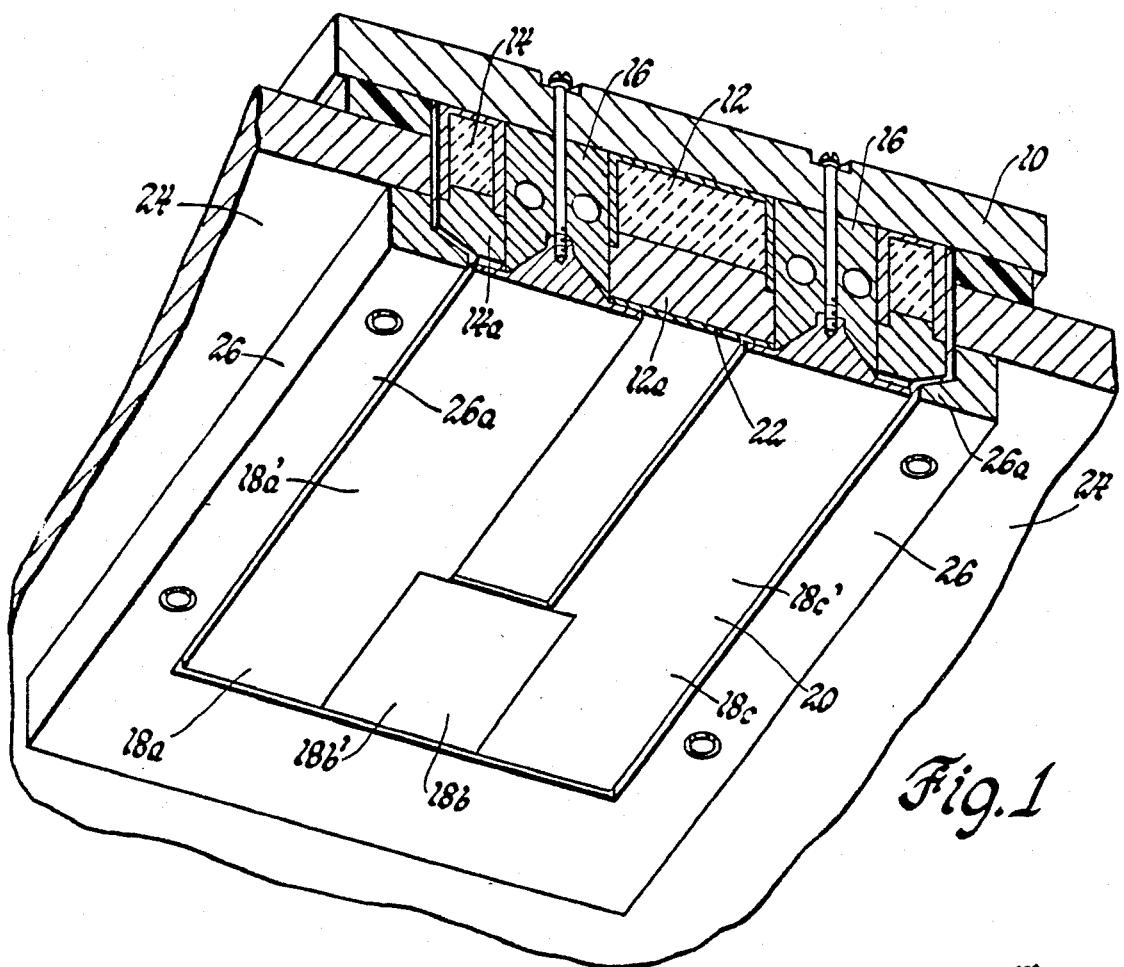
FIG. 1 shows a cross-sectional isometric view of my symmetrical planar magnetron sputtering cathode assembly described and claimed in my concurrently filed U.S. patent application Ser. No. 625,847.

This invention describes a process for making a sputtered exhaust electrode on a vitrified zirconia solid electrolyte body. In the patents previously referred to herein, the zirconia body is specifically described as a 3-5 cm long hollow thimble, made for use in an automotive exhaust gas oxygen sensor. Such a sensor thimble is shown in many of the patents to which I have herein previously referred. Hence, I did not show it again in the drawing hereof. In one embodiment, the zirconia thimble has an axial length of about 3.66 cm. It is made of zirconia that is partially or fully stabilized in its cubic form by the inclusion of about 4–8 mole percent yttria. The thimble has a taper on its outer surface of about 3 degrees - 38 minutes. Its open end has a thick radial flange that forms a circumferential shoulder on the thimble outer surface. The shoulder is about 0.25 cm wide. The flange has an axial length of about 0.6 cm between the shoulder and a small chamfer on the thimble open end. The outer diameter of the flange is about 1.3 cm. The outer surface of the thimble has a diameter of about 0.82 cm immediately adjacent the flange. The narrow end of the thimble is closed and rounded, having an external spherical radius of curvature of about 0.2 cm. Its external diameter adjacent the rounded end is about 0.3 cm. The interior surface of the hollow thimble is also tapered but slightly less than the taper on the outer surface so as to provide a thinner wall adjacent the closed end of the thimble than the thimble wall adjacent the thimble flange.

As described in the aforementioned prior patents to Gold et al, and in my U.S. Pat. No. 4,400,255 Kisner, a reference electrode is formed on the interior of the thimble before the exhaust electrode is sputtered onto the thimble exterior. The inner electrode can be formed as described in the aforementioned U.S. Pat. No. 4,264,647 Trevorrow. Trevorrow describes using a distinctive coating process and apparatus to uniformly coat platinum ink on the inner surface of the thimble. The platinum ink is then dried and the thimble heated in air to fire the ink to the thimble inner surface. This fired coating is the reference electrode in the resultant sensor. The axial surface on the open end of the thimble also receives a fired conductive coating, that intersects with the reference electrode, to facilitate making electrical contact with the reference electrode in the resultant sensor. Because of this end coating, the reference electrode is in low electrical resistance electrical contact with a conductive support surface when the thimble rests on its open end, i.e. upstands, on a horizontal conductive support surface.

It should be understood that this invention is primarily intended for simultaneously sputter coating outer electrodes onto several hundred zirconia thimbles at the same time. I contemplate upstanding about 418 thimbles on a pallet such as described in my U.S. Pat. No. 4,400,255 Kisner. The pallet is then passed through a sputtering zone beneath my improved cathode assembly. The cathode assembly is the one shown in the drawing hereof, and described in my co-filed U.S. patent application Ser. No. 625,847. One unique feature of my cathode assembly is that it includes very strong magnets. Magnets that are very much stronger than the magnets included in the commercially available planar cathode assembly previously used. For example, the planar assembly previously used had an actually measured magnetic field strength across the target face of only about 300 gauss midway between magnet pole pieces. In my improved cathode assembly, I use magnets producing a field strength of 3000 gauss measured at and perpendicular to the pole piece face. This produces an actually measured field strength across the unsputtered target face of about 750 gauss parallel to the target face and midway between magnet pole pieces.

Another important feature of my cathode assembly is that it has no signficant electron shielding. The previously used planar target did not have signficant electron shielding either. On the other hand, the much stronger magnets used in my improved cathode assembly produce a much stronger electron flux, that bombards the substrates during sputter coating. Thus, substrates are much more strongly heated with my cathode assembly, since electron heating is by far the most dominant heating effect during sputtering. Ordinarily, one would consider such a bombardment objectionable, particularly in the degree such as produced by my cathode assembly. Consequently, the absence of electron shields in my cathode assembly is quite notable. A dark space shield is used to prevent sputter erosion of the outer magnet subassembly surface. However, it does not extend far enough over that surface to significantly trap electrons.

Figure 2:
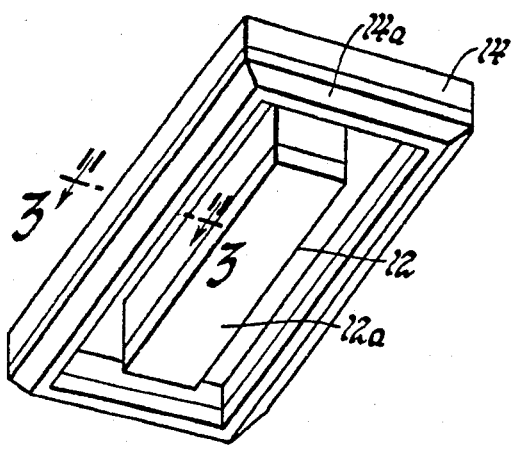
FIG. 2 shows an isometric view of the two magnet assemblies of the cathode assembly of FIG. 1.
Figure 3:
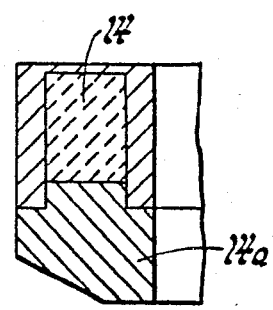
FIG. 3 shows a cross-sectional view of one of the magnet assemblies taken along the line 3—3 of FIG. 2.

Reference is now made to FIGS. 1–3 for a brief description of my unique cathode assembly. It includes a flat base plate 10, a bar magnet 12 and a surrounding frame magnet 14 occupying the same series of contiguous horizontal planes. Each of the bar magnet 12 and the frame magnet 14 are of samariumcobalt, and respectively have thick low reluctance stainless steel portions 12a and 14a serving as magnet pole pieces. The sides and top of each magnet are covered with a thin, high reluctance stainless steel layer with the top being quite thin to provide lower loss. A copper frame-like water cooling member 16 is nested between the bar magnet 12 and the frame magnet 14. Center magnet 12 and its encircling frame magnet 14 have the same surface areas on top and on the bottom. However, matching surface areas is not necessary unless the poles are saturated with magnetic field. As previously mentioned, each magnet has a magnetic strength of about 3000 gauss at its pole. This provides a magnetic field strength on the target face 20 and parallel to the target face, midway between the pole pieces 14a and 12a, of about 750 gauss.

The frame-like cooling member 16 supports four platinum target elements 18a, 18b, 18c and 18d (not shown), that are symmetrical along the length of the assembly. Each target element has a cross-section analogous to the target erosion pattern. Target elements 18a–18d are arranged on the cooling member to form a substantially continuous rectangular ring that forms the target face 20 on the lower surface, i.e. working face, of the cathode assembly. In the embodiment of the invention hereinafter described, the target face 20 is a rectangular planar ring having inner dimensions of about 11 inches long and 1 inch wide, and outer dimensions of 15 inches long and 5 inches wide. This provides a target face having an approximate area of 64 inches$^2$. Elements 18a–18d are affixed to the cooling frame member 16 by means of sealed bolts extending through both the cooling member 16 and base plate 10.

Figure 4:
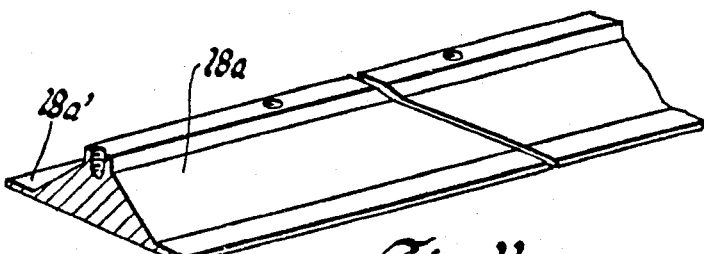
FIG. 4 shows a partly broken-away isometric view of an alternate target for the cathode assembly of FIG. 1.

Sputter erosion in the central part of the cathode working face is minimal. However, to insure utmost purity of the resultant platinum coating and to protect the magnet pole piece 12a, I prefer to cover the magnet pole piece 12a with a thin sheet of platinum 22. I use a sheet about 0.02 inch thick. Sputter erosion of the outer magnet pole piece 14a is prevented by a circumferential dark space shield 26 on the upper wall 24 of the sputtering chamber cooperating with the outer flanges 18a', 18b', 18c' and 18d' (not shown) on the target elements 18a-18d. FIG. 4 shows that the long target piece 18a could, in the alternative be two pieces. So could target piece 18c.

Chamber wall 24 and shield 26 would typically be at anode potential, as is usual. It should also be noted that while the shield member 26 closely encircles the frame magnet assembly 14-14a, the inward projection 26a of shield 26 does not extend appreciably over the magnet pole piece 14a. Hence, it does not prevent electrons from escaping the magnetic field of the cathode assembly and bombarding substrates during sputter coating. Accordingly, the higher energy electron flux produced by the stronger magnetic field is available for both heating and electrolysis of the zirconia thimbles as hereinafter explained.

The foregoing unique sputtering cathode assembly can be used to simultaneously sputter outer electrodes on over 400 zirconia thimbles at the same time, using a model MRC 902 DC magnetron sputtering apparatus obtained from Materials Research Corporation of Orangeburg, New York. It has a long and wide but fairly shallow rectangular vacuum chamber, containing two fixed rectangular cathode assemblies positioned over a single long rectangular anode. The anode is larger than both cathode assemblies combined and oriented with its length running along the length of the chamber. The target lengths are transverse to the chamber and anode length. I prefer to only use one target at a time, and pass the workpieces beneath it, and over the anode, during sputtering.

Thimbles are loaded onto a special masking pallet assembly that is in turn supported on a movable carrier, so that the thimbles can be passed beneath the cathode assembly during sputtering. The special masking pallet is as described in my U.S. Pat. No. 4,400,255 Kisner, to insure that the inner and outer electrodes, i.e. reference and exhaust electrodes, are not electrically shorted during sputtering. In my U.S. Pat. No. 4,400,255 I describe that the pallet and its carrier are at the same electrical potential as the anode. In the invention of this patent application, I have found that best results, particularly higher yields, are obtained if the pallet is not in low electrical resistance communication with anode potential. However, in the MRC 902 apparatus the carrier is at anode potential. Accordingly, in this invention, the pallet is not supported directly on the movable carrier. Instead, electrical insulating standoffs are interposed between the pallet and its carrier. Alternatively, the carrier could be electrically insulated in some way from the apparatus chamber walls.

The pallet includes a masking plate having a plurality of apertures for receiving the flange of the sensor thimble. The pallet masking plate has a uniform array of 418 holes. The holes are arranged in orthogonally oriented columns and rows. The holes all have a diameter of about 13.42 millimeters. Each column has 19 holes, on centers spaced 16.33 millimeters apart. Twenty-two columns are used, oriented parallel the length of the cathode assembly. Adjacent columns are staggered, with adjacent columns having their center lines spaced 13.28 millimeters apart. The thickness of the masking plate is less than the axial length of the thimble so as to prevent a low resistance electrical connection from occurring between it and the exhaust electrode during sputtering. If the pallet and outer electrode do not electrically short during sputtering, a low resistance connection does not occur during sputtering between the inner and outer electrodes. Maintaining this electrical separation is essential to obtaining fast rich-to-lean response times in the resultant sensor.

A clean thimble is loaded in each aperture of the masking plate. Each thimble is loosely nested in its aperture. Each thimble open end is down and electrically contacting the conductive pallet supporting it. Hence, the thimble axes are vertically oriented. The pallet is then placed in a vacuum chamber for sputtering.

As previously mentioned, the thimbles have had their inner electrodes and open end coating applied and fired before they are loaded onto the sputtering pallet. As a preparation for sputtering they are cleaned. In one cleaning procedure, they are ultrasonically degreased with freon, and then heated to about 600° C. in air for about 1 hour. The sputtered outer electrode should be deposited within about 72 hours after this latter heat treatment. The fully loaded pallet is placed in a loading chamber of the MRC 902 sputtering apparatus, and the loading chamber sealed. A special carrier is provided in that apparatus for shuttling the pallet of thimbles from the loading chamber, referred to as a load-lock, into the main chamber for sputtering and then back again for unloading. A seal is provided between the loading chamber and the main chamber so that the main chamber can be substantially always maintained under sputtering atmosphere conditions or at least high vacuum conditions, except for apparatus servicing.

After sealing the loading chamber to the ambient, it is evacuated to about 100 millitorr. The seal between the loading chamber and the main chamber is opened and the pallet of thimbles is shuttled into the main chamber to a position laterally disposed from the cathode assembly shown in the drawing. The main chamber is then sealed from the loading chamber and the main chamber is pumped down to below $5 \times 10^{-6}$ torr. A flow of about 50-75 percent by volume nitrogen and 25-50 percent by volume argon, preferably 75 percent nitrogen and 25 percent argon by volume, is then introduced into the main chamber at a rate of about 75-100 cc per minute, while pumping continues. Pumping is throttled at a sufficient rate to dynamically maintain a pressure in the main chamber less than about 10 millitorr, preferably less than about 5 millitorr. Once pressure in the main chamber is stabilized, a glow discharge can be established between the cathode and anode in the chamber. Pressure is maintained at this level in this way during sputtering.

The combined height of the pallet, the nonconductive standoffs, and the carrier are sufficient to bring the closed ends of the vertically oriented thimbles to within about 2.5 cm of the target face 20 when the pallet is passed beneath the cathode assembly. I believe that it is desirable that they even be closer. However, transverse reinforcing ribs on the upper wall of the sputtering chamber in the MRC 902 sputtering apparatus do not permit signficantly closer spacing. If these reinforcing ribs were not present, I believe that a target face-thimble tip spacing as close as about 1.5 cm might be useful, even desirable.

Sputtering of the target face 20 is initiated before moving the pallet under it. Once it is stabilized, the pallet carrying thimbles are continuously moved into and through the sputtering region to the other side of the cathode assembly, outside the sputtering region. A uniform rate of about 5–10, preferably 5–6, cm per minute must be used. No supplemental heating or cooling means are used to heat or cool the pallets or thimbles. However, it should be recalled that my cathode assembly provides a significant electron radiation that heats the thimbles. The pallet movement rate is adjusted to obtain a platinum coating having an average weight of about 10 milligrams on each of the 418 thimbles being simultaneously coated in just one pass under the cathode assembly and a darkening of the thimble surface beneath the coating. Less than about 7 milligrams of electrode weight, under the conditions of this example, do not appear to provide a sufficient average improvement in electrode performance, perhaps because the darkening is not sufficient and/or the coating is not thick enough. Under the sputtering conditions described herein, more than 11 milligrams can produce negative voltages when the sensor is sensing lean air/fuel mixtures, perhaps because the coating is too thick and/or the darkening is too excessive.

In general, a platinum electrode 22 having a weight of about 10 millgrams will have a thickness of about 1.0–1.5 micrometers thick on the upper ends of the zirconia thimbles. The upper ends of the thimbles will get the greatest thickness of platinum since they are the closest to the target face 20. Side walls on the element will get a correspondingly lesser platinum deposit down to its shoulder, where the platinum increases in thickness. About 1 milligram of platinum will provide an electrode having a thickness of about 0.65–1.0 micrometer thick at a point about 0.5 cm back from the thimble closed end, along with a coating thickness of about 0.3–0.55 micrometer thick about 2 cm back from the thimble closed end.

In any event, after all 418 thimbles on the pallet have passed through the sputtering region, loosely speaking the glow discharge, the sputtering power supply is turned off and the seal opened between the main chamber and the loading chamber. The pallet can then be shuttled back into the loading chamber, the seal with the main chamber closed again, and the loading chamber backfilled with dry nitrogen to atmospheric pressure. The loading chamber can then be opened and the pallet removed.

The DC voltage and the power used with my improved cathode assembly is about the same as previously used in the aforementioned Gold et al patents and my U.S. Pat. No. 4,400,255. In other words, I prefer to adjust the power supply to provide a DC power of about 4–8 kilowatts. I presume that 7–9 kilowatts can be used without significantly affecting other parameters described herein. At an amperage of about 14 amps, this results in a DC voltage of about 500–640 volts during sputtering, even though about 800 volts may be needed to initiate the sputtering.

Gold et al and I previously disclosed using a thimble-to-target minimum spacing of at least about 3.0 cm and to about 4.5–5.0 cm. My improved sputtering cathode requires a closer spacing, in order to get the same superior results. For example, I space the tops of the thimbles only about 2.5 cm below the target face 20, and preferably not more than about 3.0 cm. If spaced further away, higher pressures are needed, more power is required to deposit the same weight of coating, and the resultant sensors tend to have non-reproducible results.

Still further, deposition in unwanted areas of the sputtering chamber tends to occur with higher power and higher pressures.

It should also be noted that the cathode assembly provides an electron bombardment of the thimbles during film deposition that I believe both heats the thimbles and provides a source of electrons for an electrolytic darkening of the thimble surface beneath the sputtered coating. With my more powerful magnetic cathode assembly, positioning of the thimble apparently is even more critical with respect to the attainment of fast responding electrodes than before.

The preferred sputtering atmoshere is 75 percent nitrogen and 25 percent argon, by volume, as previously disclosed in the aforementioned patents. On the other hand, I have found that my new cathode assembly should be used at a pressure less than about 10 millitorr, preferably at about 5 millitorr at the present time. On the other hand, pressures as low as about 1 millitorr and perhaps even 0.5 millitorr could be used so long as impurities, particularly water vapor, in the vacuum system can be kept low. For commercial production operations presumably a pressure range of about 1–5 millitorr would be most desired but 3–8 microns may end up being the most practical. I have found that sputtering rate increases with decreases in pressure. However, electron heating does not significantly increase. As pointed out in my U.S. Pat. No. 4,400,255 I believe that the presence of the high electron flux is an important factor in obtaining extremely fast responding electrodes. Depositing the platinum electrode material too fast may not permit sufficient time for both heating of the thimbles and the electrolytic darkening of the thimble surface beneath the sputtered coating that appears necessary for acquisition of the fast responding sensors. Accordingly, increasing deposition speed alone is not desirable. One must balance it with heating and electrolysis. I believe the darkening should be a blackness, not just a graying or browning of the surface, and should extend to a depth of about 0.1–0.5 millimeter. The foregoing conditions will provide such a darkening. Hence, it will provide fast responding sensors.

I have also found that with my more powerful cathode assembly, another factor must be considered. In my U.S. Pat. No. 4,400,255 I point out that the inner and outer thimble surfaces should be electrically isolated during deposition, to permit the darkening effect to occur in the proper manner. Moreover, I point out that there should be a low electrical resistance communication between the inner electrode and the anode to obtain best results. With my strong magnetic cathode assembly, I find that higher yields of satisfactorily darkened thimble surfaces are obtained if the pallet is allowed to electrically float. I suspect that the reason for this is that with no low resistance electrical connection between the anode and the pallet, charge gradually bleeds off the pallet anyway and does so uniformly. When the pallet has a low resistance electrical connection to the anode, i.e. is grounded, there may be a tendency for selected thimbles to get a considerable electrolysis and the balance not enough. This may be due to electrons seeking the lowest resistance path to the anode from among all the upstanding thimbles.

After unloading from the sputtering chamber, the thimbles can be treated in the same manner as is disclosed by Gold et al in my U.S. Pat. No. 4,400,255. For example, they can be heated for about 1 hour at about 800° C. to increase electrode adhesion. This increase in adhesion can be obtained by heating over a rather wide temperature range, extending from about 600° C. to about 1200° C. However, it should be recognized that heat treatment above 800° C. tends to sinter the porous coating which can open large holes in it as well as form isolated platinum islands. This is obviously objectionable. A porous coating of magnesium-aluminate spinel can then be flame sprayed onto the platinum electrode, leaving a portion of the electrode uncovered at or near the thimble shoulder for making a low resistance electrode connection to the outer electrode. It is recognized that flame spraying of a ceramic overcoat onto the thin electrode may drastically alter the physical appearance of the film. On the other hand, it does not appear to deleteriously affect controllability of the switching response times produced by this invention. Electrical characteristcs still remain that are attributable to the nature of the electrode as it was initially deposited.

Each coated thimble can then be assembled into a sensor, such as is illustrated in the aforementioned U.S. Pat. No. 3,844,920 Burgett et al. The resultant sensor assembly consistently exhibits fast switching response times that are similar for both rich to lean and lean to rich changes. It also exhibits a controllability closer to stoichiometry. For example, a lean-to-rich response time of less than 100 milliseconds can be consistently obtained for over 90 percent of the sensors made from such elements, even if the sensors have not been previously artifically aged in nitrogen pursuant with the aforementioned U.S. Pat. No. 4,253,934 Berg et al.

The embodiments of the invention in which an exclusive property or privilege is claimed are defined as follows:

1. In a method of DC magnetron sputtering of an exhaust electrode onto a given surface of a zirconia solid electrolyte exhaust gas oxygen sensor body, opposite from a surface on said body having a previously formed reference electrode, the improvement of:
    providing a vacuum chamber having a sputtering cathode assembly that includes a platinum target face and a magnet pair producing a field strength of at least about 500 gauss between magnet poles adjacent the target face;
    maintaining a pressure of about less than 10 millitorr in the chamber, of an atmosphere consisting essentially of more than 50% by volume of at least one member selected from the group consisting of nitrogen and oxygen and the balance an inert gas;
    disposing the sensor body on a conductive support which exposes the given surface for sputtering and permits the given and opposite surfaces to be maintained at relatively different electrical potentials, and the reference electrode being in low electrical resistance communication with the support, the support being allowed to electrically float with respect to the sputtering cathode and anode, the support being movable across the cathode target face;
    sputtering the target face at a sputtering power of about 4–9 kilowatts; and
    moving the support across the target face at a rate of about 5–10 cm per minute, effective to move the support through the sputtering region of the chamber and to concurrently deposit a porous platinum exhaust electrode onto the given surface of the sensor body and darken that surface, so that a sensor lean-to-rich response time of less than 100 microseconds and generally equal rich-to-lean response time can be obtained.

2. In a method of DC magnetron sputtering of an exhaust electrode onto a given surface of a zirconia solid electrolyte exhaust gas oxygen sensor body having an opposite surface on which a previously formed reference electrode is disposed, the improvement of:
    providing as part of an upper wall in a sputtering chamber a cathode having a platinum target face and a rectangular magnet assembly producing a field strength of at least about 700 gauss, as measured across an unsputtered target face;
    maintaining an atmosphere consisting essentially of at least about 50 percent by volume of a gas selected from the group consisting of oxygen and nitrogen and the balance an inert gas at a pressure of less than about 5 millitorr in the chamber;
    supporting the sensor body on a movable carrier with the given sensor body surface exposed for sputter coating so that during sputter coating the given surface is in lowest resistance electrical communication with the reference electrode through the sensor body itself, and with the reference electrode allowed to electrically float during sputter coating;
    locating the carrier and its so supported sensor body in the chamber laterally of the cathode for movement under the target face to an opposite lateral location with a target;
    sputtering platinum from the target face at a sputtering power of about 7–9 kilowatts; and
    while so sputtering, moving the carrier from the one chamber location to the other, at a substantially constant rate of about 8–10 cm per minute while the sensor body is directly under the target face, to deposit a porous platinum exhaust electrode onto the given sensor body surface and concurrently blacken that surface whereby a sensor lean-to-rich response time of less than 100 microseconds and generally equal rich-to-lean response time is obtained.

3. In a method of DC magnetron sputtering of an exhaust electrode onto a given surface of a zirconia solid electrolyte exhaust gas oxygen sensor body, opposite from a surface on said body having a previously formed reference electrode, the improvement of:
    providing a vacuum chamber having a sputtering cathode assembly that includes a platinum target face and a magnet pair producing a field strength of at least about 500 gauss between magnet poles adjacent the target face;
    maintaining a pressure of about 1–8 millitorr in the chamber, of an atmoshere consisting essentially of more than 50% by volume nitrogen and the balance argon;
    disposing the sensor body on a conductive support which exposes the given surface for sputtering and permits the given and opposite surfaces to be maintained at relatively different electrical potentials, and the reference electrode being in low electrical resistance communication with the support, the support being allowed to electrically float with respect to the sputtering cathode and anode, the support being movable across the cathode target face;
    sputtering the target face at a sputtering power of about 4–9 kilowatts; and
    moving the support across the target face at a rate of about 8–10 cm per minute, effective to produce a fast responding catalytic electrode by moving the support through the sputtering region of the chamber and thereby concurrently deposit a porous platinum exhaust electrode onto and blacken the given surface of the sensor body to a depth of less than about 1 micrometer.

4. In a method of DC magnetron sputtering of an exhaust electrode onto a given surface of a zirconia solid electrolyte exhaust gas oxygen sensor body having an opposite surface on which a previously formed reference electrode is disposed, the improvement of:

providing as part of an upper wall in a sputtering chamber a cathode having a platinum target face and a rectangular magnet assembly producing a field strength of at least about 700 gauss, as measured across an unsputtered target face;

maintaining a pressure of about 1–5 millitorr in the chamber, of an atmosphere consisting essentially of about 50–75 percent by volume of nitrogen and about 25–50 percent by volume argon;

supporting the sensor body on a movable carrier with the given sensor body surface exposed for sputter coating, in relatively high resistance electrical communication with the reference electrode, and with the reference electrode allowed to electrically float during sputter coasting;

locating the carrier and its so supported sensor body in the chamber laterally of the cathode for movement under the target face to an opposite lateral location with a target to give a minimum spacing of about 2.0–3.0 cm from the sensor body to the target face while the carrier is directly under the target face;

sputtering platinum from the target face at a sputtering power of about 7–9 kilowatts; and while so sputtering, moving the carrier from the one chamber location to the other, at a substantially constant rate of about 8–10 cm per minute while the sensor body is directly under the target face, to deposit a porous platinum exhaust electrode onto the given sensor body surface and concurrently blacken that surface to a depth of at least about 0.1 micrometer.

* * * * *